United States Patent
Marcotte et al.

(10) Patent No.: US 7,532,746 B2
(45) Date of Patent: May 12, 2009

(54) SYSTEM AND METHOD FOR LOCATING AND ACCESSING A BLOOD VESSEL

(75) Inventors: Ronald Marcotte, New Gloucester, ME (US); Mark Arsenault, Sanford, ME (US); Dominic Pelletier, Raymond, ME (US); Walter Hebold, Raymond, ME (US); Milton Waner, New York, NY (US); Louis Fink, Little Rock, AR (US)

(73) Assignee: Vue Tek Scientific, LLC, Gray, ME (US)

( * ) Notice: Subject to any disclaimer, the term of this patent is extended or adjusted under 35 U.S.C. 154(b) by 764 days.

(21) Appl. No.: 11/022,569

(22) Filed: Dec. 22, 2004

(65) Prior Publication Data
US 2005/0281445 A1    Dec. 22, 2005

Related U.S. Application Data

(63) Continuation-in-part of application No. 10/760,051, filed on Jan. 16, 2004, now abandoned.

(51) Int. Cl.
*G06K 9/00* (2006.01)
(52) U.S. Cl. .................................................. 382/128
(58) Field of Classification Search ................. 382/128; 600/473
See application file for complete search history.

(56) References Cited

U.S. PATENT DOCUMENTS

| | | | | |
|---|---|---|---|---|
| 5,781,913 | A * | 7/1998 | Felsenstein et al. | 345/169 |
| 6,032,070 | A * | 2/2000 | Flock et al. | 600/473 |
| 7,072,096 | B2 * | 7/2006 | Holman et al. | 359/298 |

OTHER PUBLICATIONS

Digital Image Processing, 2/E, by Gonzales et al, Publisher: Prentice Hall, copyright 2002; ISBN: 0201180758.*

* cited by examiner

*Primary Examiner*—Tom Y Lu
(74) *Attorney, Agent, or Firm*—Michael J. Persson; Lawson & Persson, P.C.

(57) ABSTRACT

An imaging system for locating subcutaneous blood vessels and a method for locating subcutaneous blood vessels using the system. The system includes at least one infrared emitter an infrared detector, a computing unit that enhances images and outputs enhanced images in substantially real time, a display device for displaying enhanced images, and a power source. The method includes the steps of preparing a body target area, putting on the headset, powering up the system, locating a target blood vessel, inserting a needle into the target blood vessel, and performing the medical procedure.

36 Claims, 6 Drawing Sheets

SYSTEM AND METHOD FOR LOCATING AND ACCESSING A BLOOD VESSEL

CLAIM OF PRIORITY

This application is a Continuation-in-Part of U.S. patent application Ser. No. 10/760,051, filed Jan. 16, 2004 now abandoned.

FIELD OF THE INVENTION

The present invention relates generally to the non-invasive viewing of surface and subsurface blood vessels by use of an infrared imaging. In particular, the present invention relates to an imaging system for viewing and accessing subcutaneous blood vessels and a method of use thereof.

BACKGROUND OF THE INVENTION

Intravenous (IV) access is the single most frequently performed invasive medical procedure in the world today. Though IV is generally considered routine, there are a number of situations in which inhibited IV access can be painful, traumatic, or even dangerous to patients. These include conditions in which subcutaneous blood vessels are difficult to locate because of patient characteristics or environmental conditions. For example, in battlefield conditions, where lighting is limited, it may be difficult, if not impossible, to locate subsurface blood vessels for injection. Easy IV access is especially critical in emergency situations in which a patient's life may depend on immediate IV access and "first-stick" accuracy.

Medical practitioners often encounter difficulty in gaining IV access in a significant portion of the patient population for which subsurface blood vessels are obscured. Such patients include obese patients, darkly pigmented patients, neonates (infants from birth to four weeks of age), children under four years of age, patients experiencing lowered blood pressure, patients who have collapsed veins, and patients requiring IV access in a minor or obscured blood vessel. Difficulties arising in these populations are demonstrated by the numbers: first-stick success rates in children and infants are currently 30%, which indicates that for 70% of the time, IV access in these populations requires more than one stick attempt. In neonates, more than 90% of IV catheters must be removed prematurely, mainly because of the improper placement of the catheters. Difficulties with IV access are encountered not only in locating the subsurface blood vessels, but also in complications that arise from improper insertion of needles or catheters in target blood vessels. Such complications include infiltration, thrombophlebitis, and infection of the IV access site.

It should be noted that children who have obscured blood vessels might lie in operating rooms for longer than 30 minutes, while medical practitioners attempt to find a blood vessel suitable for successful IV access. With the cost of operating room time approximately $14,000 per hour, delayed IV access can significantly increase the expense of both operating and office-based medical procedures.

IV access is especially critical in emergency situations when first stick accuracy can be life saving. A loss of time or inability to obtain IV access can mean the difference between life and death or, at a minimum, cause significant physical and psychological trauma. Further complicating matters, loss of patient blood and blood pressure in trauma situations can make locating subsurface blood vessels extremely difficult.

In cases where catheters, cannulas, and/or IV drips are used in patient treatment, these devices typically remain in a patient's blood vessel for a long period of time. However, in order to prevent infection, the devices are generally relocated to new body areas every 48 to 72 hours. Constant relocation of these devices over a long-term hospital stay may result in a need for medical practitioners to access less-optimal blood vessels, after more prominent blood vessels have been used. Often, these less prominent blood vessels can not easily be found by visual and tactile clues, and accessing them may require multiple sticks to the patient, which thereby causes the patient physical and emotional pain and trauma. Inhibited IV access can also subject medical practitioners to legal liability risk, by contributing to the complications associated with improper, ineffective, or delayed IV access.

IV location and access is both a visual and a tactile process. Traditional methods of IV location and access rely on the medical practitioner using his/her eyes and both hands to clean the target area, apply a tourniquet, locate the blood vessel by palpating the target area, and apply the hypodermic needle. For the sake of safe and efficient patient treatment, it is critical that the hands and eyes of the medical practitioner gaining IV access not be hindered in any way.

Medical practitioners gain proficiency at IV location and access through a process of learning and continued practice. To ensure a high standard of healthcare and patient safety, it is imperative that medical practitioners do not attempt to gain IV access before they are adequately trained. Unfortunately, traditional methods of IV location and access may require years of trial-and-error practice and thereby delay critical healthcare, which increases healthcare costs and possibly jeopardizes patient health. Any advancement in healthcare practices that reduces the amount of training time required for proficiency in gaining skill at IV access could contribute significantly to improved patient care.

In order to provide the highest standard of care while reducing the cost of healthcare, it is imperative that medical practitioners locate and gain access to subsurface blood vessels in a rapid and accurate manner. Simplified IV location and access can help to save lives in emergency situations, avoid the trauma of multiple sticks in situations in which patients' vessels are difficult to locate, reduce the number of complications that stem from improperly inserted hypodermic needles and IVs, and reduce costs of medical procedures, by speeding up a critical bottleneck in many medical procedures: IV access. Therefore, what is needed is a hands-free device that allows medical practitioners to rapidly and accurately locate subsurface blood vessels for IV access.

As of late, apparatus have developed that help medical personnel more accurately locate blood vessels. For example a system and method for locating subcutaneous blood vessels via IR enhancement is described in U.S. Pat. No. 4,817,622, entitled, "Infrared imager for viewing subcutaneous location of vascular structures and method of use," in which a human appendage, typically the inside of the elbow, is illuminated with an IR source, for example, at least one incandescent light bulb. A video camera for producing a video image and immediately overlying monitor for displaying the video image is utilized to look at the flesh. The camera is sensitive to IR radiation. A video display in which IR absorbing or scattering contrasting portions of the flesh are highlighted, for example, hard-to-find veins for inserting needles. A contrast enhancing circuit is included, which discloses amplifying the video information with high contrast enhancement of the video. Adaptation of the disclosed circuit to conventional TV charge coupled device cameras and monitors is illustrated with compensation of horizontal sweep to even image background, intensity averaging line-to-line for vertical image uniformity, and display of image contrasts, in a log amplification format. While the '622 patent describes an IR blood vessel viewer, the '622 patent utilizes an analog signal processor, which is not adequate for supporting the digital algorithms needed for true image enhancement and visualization.

More recently, U.S. Pat. No. 5,519,208, purports to describes a method and apparatus for gaining intravenous access that includes a source of radiation for irradiating an area of the patient with radiation having a wavelength that is absorbed in areas containing veins and reflected in all other areas. The reflected radiation is then read and the output displayed. Using this technique, venous structures appear as dark lines on the display, enabling a user to position the tip of a hypodermic needle at an appropriate location for drawing blood.

Along similar lines, U.S. Pat. No. 6,032,070, purports to describe a system and method to view an anatomical structure such as a blood vessel in high contrast with its surrounding tissue. The system and method may be used to produce an image of an anatomical structure using reflected electromagnetic radiation singularly scattered from target tissue. The system and method purport to provide improved contrast between any anatomical structure and its surrounding tissue for use in any imaging system.

Likewise, U.S. Pat. No. 6,230,046, purportedly discloses a system and method for enhancing visualization of veins, arteries or other subcutaneous natural or foreign structures of the body and for facilitating intravenous insertion or extraction of fluids, medication or the like in the administration of medical treatment to human or animal subjects. The system and method include a light source for illuminating or transilluminating the corresponding portion of the body with light of a selected wavelengths and a low-level light detector such as night vision goggles, a photomultiplier tube, photodiode or charge coupled device for generating an image of the illuminated body portion, and optical filter(s) of selected spectral transmittance which can be located at the light source(s), detector, or both.

The above referenced patents are illustrative of attempts to demarcate blood vessels from surrounding tissue. The systems and methods of the described patents are non-invasive and, most importantly, provide the near "real time" visualization of the image necessary for these devices to serve their practical purpose. However, because of the need to provide near "real time" images, these devices primarily depend on raw images, or images marginally enhanced by traditional analog means, which are of relatively poor quality for venepuncture accuracy. Therefore, there is a need not only for a device for visualizing subsurface blood vessels, but also a system and method for vascular image location, image enhancement, and hands-free manipulation, for quick and accurate IV access.

Therefore, there is a need for an improved system and method for locating and accessing a target blood vessel that that has the vein enhancing features of the prior art devices discussed above, but produces high quality images in near "real time" such that the system may be used by medical personnel during venepuncture, that allows target blood vessels to be more accurately and rapidly located than is possible using current systems and methods, that allows target blood vessels to be more easily located in difficult conditions and body types (e.g., obese patients, dark pigmentation skin, neonates, collapsed veins, low lighting), that reduces patient pain and trauma, both emotionally and physically; and that allows minimally trained medical staff to provide IV access.

SUMMARY OF THE INVENTION

The present invention is an imaging system for locating subcutaneous blood vessels and a method for locating subcutaneous blood vessels using the system. In its most basic form, the system includes at least one infrared emitter an infrared detector, a computing unit, a display device, and a power source.

The infrared emitter is, or emitters are, configured to illuminate a region under a surface of skin with waves of infrared light. The infrared detector, preferably a CMOS camera, is configured to accept waves of infrared light reflected from the region under the surface of the skin and includes an output for outputting a signal corresponding to unenhanced image data. The computing unit includes an input for accepting the unenhanced image data, a memory, means for enhancing and outputting result images in which enhanced images of blood vessels are shown within the images of the region under the surface of the skin, and an output for outputting the enhanced images in substantially real time. The display device inputs the enhanced images from output of the computing unit and displays the enhanced images. Finally, the power source is in electrical communication with the infrared emitter, the infrared detector, the computing-unit and the display device and provides power thereto.

In the preferred embodiment of the system, the means for enhancing and outputting result images includes a digital signal processing unit programmed with computer program means for enhancing and outputting result images at a rate of at least five frames per second. The preferred computer program means includes program means for Gaussian blurring a raw image with a kernel radius of 15, program means for adding an inverse Gaussian-blurred image to the raw image, and program means for level adjusting a result image to use an entire dynamic range.

The preferred system includes a headset to which the two arrays of infrared emitters, infrared detector, computing unit, display, and power source are attached. The headset preferably includes a pair of extension arms extending therefrom and a mounting surface pivotally attached to the pair of extension arms. In this arrangement, the two arrays of light emitting diodes and the infrared detector are attached to the mounting surface. The display is preferably disposed upon the headset such that a user is able to view both the display and the surface of the skin without removing the headset.

The preferred light emitting diodes are surface mounted light emitting diodes comprising integral micro reflectors. At least one light shaping diffuser is preferably disposed between the arrays of surface mounted light emitting diodes and the surface of the skin. Such a diffuser is preferably-integral to the light emitting diodes, but may be a separate diffuser. At least one first polarizing filter is preferably disposed between the surface mounted light emitting diodes and the surface of the skin, and at least one second polarizing filter is preferably disposed between the surface of the skin and the infrared detector. The polarizing filters preferably act to cross polarize the light, but may provide any arrangement of polarization, or be eliminated completely.

The infrared detector is preferably a CMOS camera adapted to generate digital data corresponding to the waves of infrared light reflected from the subcutaneous blood vessels located in the region under the surface of the skin. The CMOS camera may include a high band pass filter adapted to filter out substantially all light outside of an infrared spectrum, or may be adapted to receive both infrared and visible spectrum light. A camera lens is preferably disposed between the surface of the skin and the CMOS camera in order to adjust the focal length of the image. However, in embodiments in which a specialized CMOS camera having the proper focal length is used, or those in which the images are digitally adjusted for proper visualization on the display unit, the camera lens is eliminated altogether.

The preferred display is an LCD screen type display having a pair of LCD screens. At least one optical lens is preferably disposed between the LCD screens and a pair of eyes of a user to adjust for differences between the enhanced image an the unenhanced image viewed directly the user. However, in embodiments in which a in which a specialized display, having the proper focal length is used, or those in which the images are digitally adjusted for proper visualization on the display unit, the optical lens is eliminated altogether.

Finally, the preferred computing unit includes a digital signal processing unit and image data storage means for storing a multiple images for future viewing. The preferred computing unit also includes an interface for inputting data from a data input and and outputting data to a data output device.

In its most basic form, the method of using an imaging system to aid in an insertion of a hypodermic needle into a blood vessel during a performance of a medical procedure includes steps of preparing a body target area, putting on the headset, powering up the system, locating a target blood vessel, inserting a hypodermic needle into the target blood vessel, and performing the medical procedure.

In the preferred method, the infrared detector of the system is a camera and the step of locating a target blood vessel includes the steps of directing incident light from the infrared emitters on the target area of the surface of the skin, and viewing the target area on the display. In embodiments in which the system includes an optical lens, the step of locating a target blood vessel may include the steps of viewing the image of the target area of the skin as displayed on the display, viewing the unenhanced image on the target area of the skin and adjusting the optical lens to correct the enhanced image displayed on display for depth perception differences between the enhanced image and the unenhanced image. In still other embodiments, the step of locating a target blood vessel includes the steps of viewing the image of the target area of the skin as displayed on the display, viewing the unenhanced image on the target area of the skin and adjusting the display to correct the enhanced image displayed on display for depth perception differences between the enhanced image and the unenhanced image.

The preferred embodiment of the method includes the step of optimizing the system. In some embodiments, the optimizing step includes using a data input to specify an enhancement algorithm stored in memory to be used by the digital signal processor to generate the enhanced image. In some such embodiments, the enhancement algorithm is selected based upon a factor selected from a group consisting of a body type, pigmentation, and age of the patient. In other embodiments, the optimizing step includes the step of using the data input to adjust an intensity level of the infrared emitter or emitters.

In embodiments of the method in which the hypodermic needle is an infrared viewable hypodermic needle, the step of inserting a hypodermic needle into the target blood vessel may also include the step of viewing the infrared viewable hypodermic needle on the display during and after insertion into the target blood vessel.

Finally, some embodiments of the method also include the steps of removing the headset and powering off the system.

Therefore, it is an aspect of the invention to provide an improved system and method for locating and accessing a target blood vessel that that produces high quality images in near "real time" such that the system may be used by medical personnel during venepuncture.

It is a further aspect of the invention to provide an improved system and method for locating and accessing a target blood vessel that allows target blood vessels to be more accurately and rapidly located than is possible using current systems and methods.

It is a further aspect of the invention to provide an improved system and method for locating and accessing a target blood vessel that allows target blood vessels to be more easily located in difficult conditions and body types (e.g., obese patients, dark pigmentation skin, neonates, collapsed veins, low lighting).

It is a further aspect of the invention to provide an improved system and method for locating and accessing a target blood vessel that reduces patient pain and trauma, both emotionally and physically.

It is a still further aspect of the invention to provide an improved system and method for locating and accessing a target blood vessel that allows minimally trained medical staff to provide IV access.

These aspects of the invention are not meant to be exclusive and other features, aspects, and advantages of the present invention will be readily apparent to those of ordinary skill in the art when read in conjunction with the following description, appended claims and accompanying drawings.

DETAILED DESCRIPTION OF THE INVENTION

Figure 1:
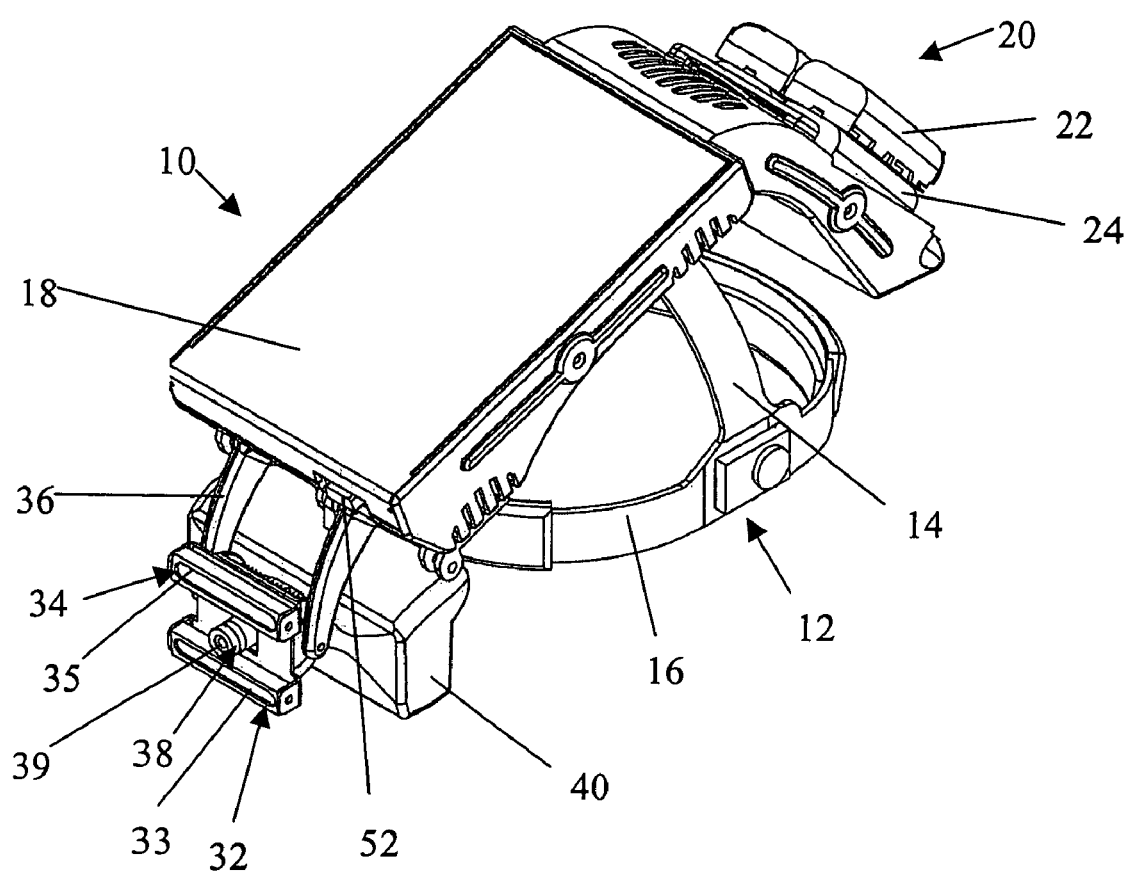
FIG. 1 is a front isometric view of the preferred embodiment of the system of the present invention.
Figure 2:
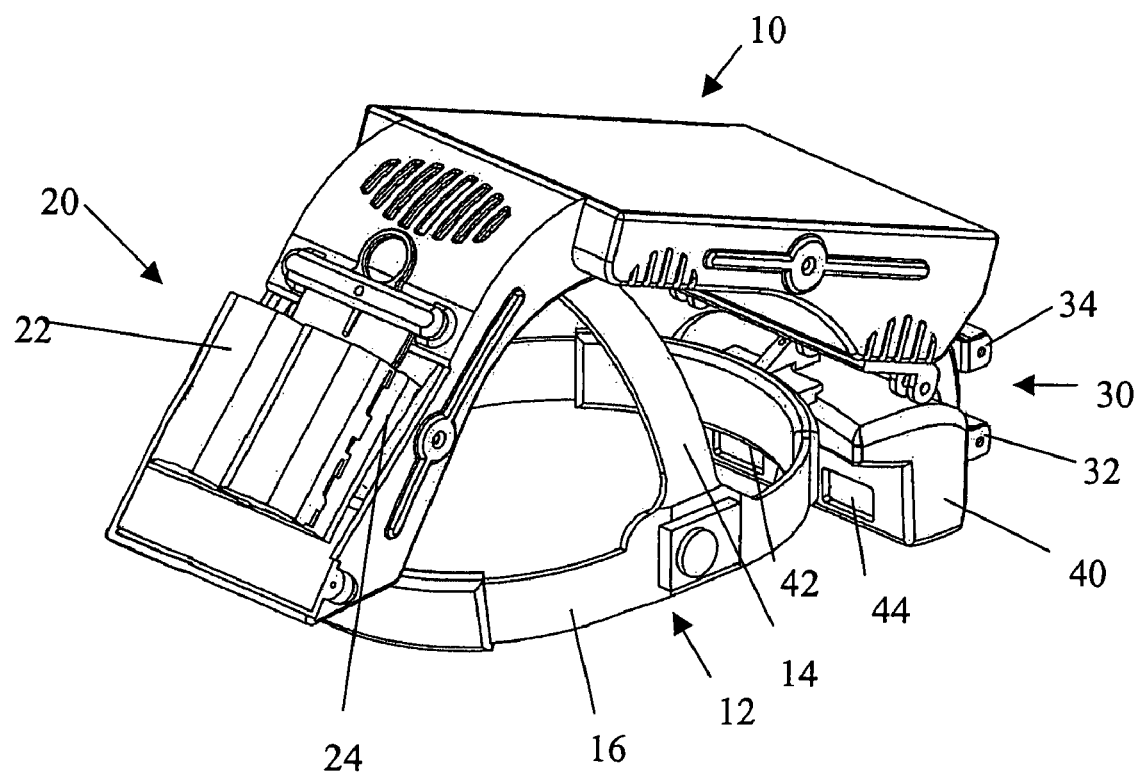
FIG. 2 is a rear isometric view of the preferred embodiment of the system of the present invention.
Figure 3:
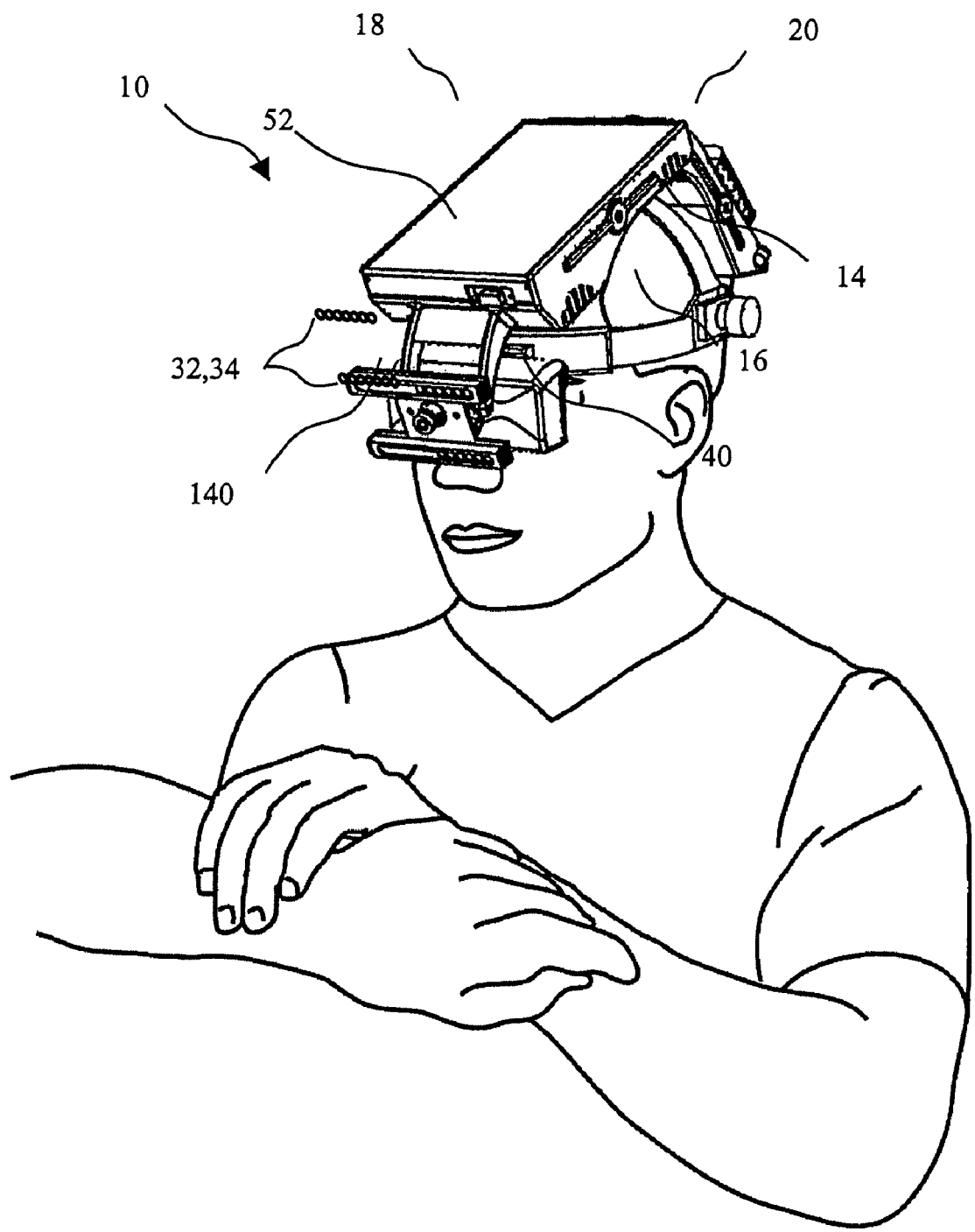
FIG. 3 is an isometric view of the preferred embodiment of the system worn on the head of a user.

FIGS. 1-3 show the preferred embodiment of the imaging system 10 of the present invention. The preferred embodiment of the system 10 includes a headset 12 to which all system components are attached. The preferred headset 12 includes two plastic bands 14,16; a vertical band 14 connected to sides of a horizontal band 16. The vertical band 14, holding most of the system components, generally acts as a load-bearing member, while the horizontal band 16 is adjustable such that it snugly fits about the forehead of the person using the system.

A pivoting housing 18 is attached to the headband 12. The housing 18 is substantially hollow and is sized to house and protect a headset electronics unit 120 disposed therein.

Attached to the housing 18 are a power supply 20, an image capture assembly 30, and an enhanced image display unit 40.

The power supply 20 for the headset electronics unit 120 preferably includes two rechargeable lithium ion batteries 22, which are connected to the electronics unit via a pair of battery terminals 24 attached to the rear of the housing 18. The rechargeable lithium ion batteries 22 are preferably of the same type commonly used with video camcorders, as these are readily available, are rechargeable without fear of memory problems, make the unit completely portable, and will provide sufficient power to the headset electronics unit 120 when two such batteries 22 are used. However, it is recognized that any power supply 20 known in the art to supply power to electronics, such as alternating current power plugs, may be employed to achieve similar results.

The image capture assembly 30 is powered thorough the headset electronics unit 120 and includes a pair of infrared emitters 32, 34, and a camera 38, or other infrared detector, disposed between the infrared emitters 32,34. The infrared emitters 32,34 and camera 38 are preferably attached to a common mounting surface 31 and are pivotally connected to a pair of extension arms 36 that extend from the housing 18. Mounting in this manner is preferred as it allows the emitters 32, 34 and camera 38 to be aimed at the proper target, regardless of the height or posture of the person wearing the headset. However, it is recognized that both could be fixedly attached to the headset, provided the relationship between the emitters 32, 34 and camera 38 remained constant.

The infrared emitters 32, 34 of the preferred embodiment are surface mount LEDs (light emitting diodes) that feature a built-in micro reflector. Light emitting diodes are particularly convenient when positioned about the head because they are found to generate less heat then conventional bulbs and do not require frequent changing. Further, surface mount LED's that emit infrared light through light shaping diffusers to provide uniform light and are readily adapted for attachment to a variety of other flat filter media. The preferred infrared emitters 32, 34 each utilize a row, or array, of such LED's in front of which is disposed a light shaping diffuser (not shown). Such emitters 32, 34 may be purchased from Phoenix Electric Co., Ltd., Torrance, Calif. First polarizing filters 33, 35 are mounted in front to the light shaping diffusers of each of the infrared emitters 32, 34. These polarizing filters 33, 35 are preferably flexible linear near-infrared polarizing filters, type HR, available from the 3M Corporation of St. Paul, Minn. In operation, the LED's are powered through the headset electronics unit 120 and emit infrared light, which passes through the light shaping diffuser 205 and the first polarizing filters 33, 35 to produce the polarized infrared light 215 that is directed upon the object to be viewed.

The camera 38 is adapted to capture the infrared light 230 reflected off of the object to be viewed and to provide this "raw image data" to the headset electronics unit 120. The preferred camera 38 is a monochrome CMOS camera that includes a high pass filter (not shown) that filters out all light outside of the infrared spectrum, including visible light. A CMOS camera is preferred as it produces pure digital video, rather than the analog video produced by the CCD cameras disclosed in the prior art, and is, therefore, not susceptible to losses, errors or time delays inherent in analog to digital conversion of the image. The CMOS camera is may be any number of such cameras available on the market, including the OMNIVISION® model OV7120, 640×480 pixel CMOS camera, and the MOTOROLA® model XCM20014. In the test units, the OMNIVISION® camera was used with good success. However, it is believed that the MOTOROLA® camera will be preferred in production due to its enhanced sensitivity to infrared light and the increased sharpness of the raw image produced thereby.

A camera lens 240 is preferably disposed in front of the camera 38. This camera lens 240 is preferably an optical lens that provides an image focal length that is appropriate for detection by the camera 38, preferably between six inches and fourteen inches, eliminates all non-near IR light, and reduces interference from other light signals. The preferred camera lens 240 is not adjustable by the user. However, other embodiments of the invention include a camera lens 240 that may be adjusted by the user in order to magnify and/or sharpen the image received by the camera 38. Still others eschew the use of a separate camera lens 240 completely and rely upon the detection of unfocused light by the camera 38, or other infrared detector.

A second linear polarizing filter 39 is disposed in front of the lens 240 of the camera 38. This second polarizing filter 39 is preferably positioned so as to be perpendicular to the direction of polarization through the first polarizing filters 33, 35 in front of the infrared emitters 32, 34, effectively cross polarizing the light detected by the camera 38 to reduce spectral reflection. The polarizing filter 39 was selected for its high transmission of near-infrared light and high extinction of cross-polarized glare. Such polarizer may be purchased from Meadowlark Optics, Inc. of Frederick, Colorado under the trademark VERSALIGHT®.

The camera 38 is in communication with the headset electronics unit 120 and sends the raw image data to the unit for processing. The headset electronics unit includes the electronics required to supply power from the power supply 20 to the image capture assembly 30, and an enhanced image display unit 40, and the compatible digital processing unit 122 which accepts the raw image data from the camera 38, enhances the raw image, and sends an output of the enhanced image to the enhanced image display unit 40 and, optionally, to an interface 52. In the preferred embodiment, this interface 52 is standard VGA output 52. However, interface 52 may be any electronic data I/O interface capable of transmitting and receiving digital data to and from one or more input or output devices, such as an external monitor, external storage device, peripheral computer, or network communication path.

The preferred digital signal-processing unit 122 is a digital media evaluation kit produced by ATEME, Ltd. SA, Paris, France under model number DMEK6414, which uses a Texas Instruments TMS320C6414 digital signal processor. This processing unit 122 is preferably programmed with an embodiment of the computer program means described in the applicants' co-pending U.S. patent application Ser. No. 10/760,051, in order to enhance the images. The image enhancement algorithms embodied in the computer program means utilize several elemental processing blocks, including (1) Gaussian Blurring a raw image with a kernel radius of 15, (2) adding the inverse Gaussian-blurred image to the raw image, and (3) level adjusting the result to use the entire dynamic range. Image enhancement is performed in a series of steps, which are coded into a computer program that runs on digital signal processor 120. The programming languages are typically C language and assembly language native to digital signal processor 120. An example algorithm is as follows:

```
ON device startup
BEGIN
    Perform Initialization of Blur Kernel
END
WHILE device = ON
BEGIN
    Acquire digital image data from the camera into RAM buffer
    Save non-enhanced copy of the image data into another RAM buffer
    Perform 2D transform of image data in first RAM buffer into the
    frequency domain
```

-continued

>     Perform smoothing of transformed image data USING Blur Kernel
>     Perform 2D inverse transform of smoothed image data into
>         the spatial domain
>     Perform inversion of the smoothed image data
>     Perform add the inverted image data to the non-enhanced copy
>         of the image data
>     Perform contrast stretching
>     Perform gamma enhancement.
>     Send the enhanced image data to the display buffer
> END However, it is understood that other systems may use different means for similarly enhancing such images in near real-time and, therefore, it is understood that all embodiments of the invention need not include this program product or perform the methods described in the above referenced patent application.

The enhanced image is outputted from the processing unit to the enhanced image display unit 40. The preferred display unit 40 is distributed by i-O Display Systems of Sacramento, Calif., under the trademark I-Glasses VGA. This display unit 40 includes a binocular display that includes a pair of LCD screens in front of which are disposed a pair of optical lenses 42, 44 that allow the focal length to be adjusted for ease of viewing. The preferred an optical lenses 42, 44 provides image depth perception compensation to the user when the system 10 is used in a bifocal mode. That is, when the user views the body target area via display 150, the optical lenses 42, 44 ensure that the image appears similarly sized and distanced as when the user views the target area without using display 40. However, it is understood that a monocular display unit 40 having no such focal length adjustment could likewise be used. The preferred display unit 40 also includes an on-screen display that is not currently used, but may be used in the future to show what enhancement option has been chosen by the user.

The system 10 may be used in a total immersion mode, in which the user focuses on the target area by using exclusively display 40. Alternatively, the system 10 may be used in a bifocal mode, in which the user views the body target area via a combination of display 40 and the naked eye. In bifocal mode, the user alternates between viewing the enhanced and non-enhanced image views of the body target area, by directing his/her gaze upward to display 40 or downward toward the body target area and away from display 150.

Figure 4:
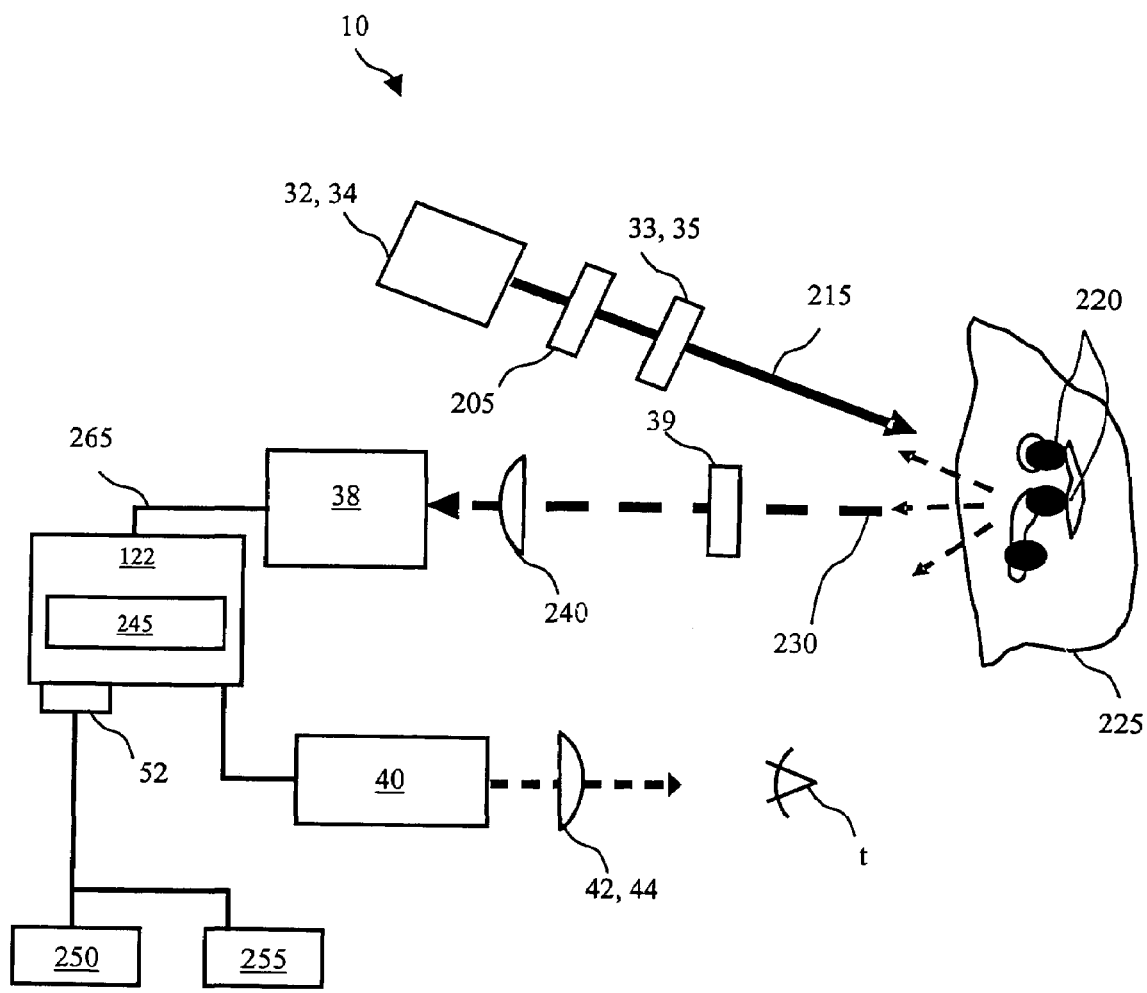
FIG. 4 is a diagram illustrating the operation of one embodiment of the infrared imaging system of the present invention to detect subcutaneous blood vessels.

FIG. 4 illustrates one embodiment of the infrared imaging system 10 used to view subcutaneous blood vessels 220, such as arteries, veins, and capillary beds, which are present under the surface 225 of normal human skin. The infrared imaging system 10 described in connection with FIG. 4 includes all of the features of the preferred embodiment described above, in addition to including a camera lens 240, image data storage means 445, a data input 250, and data output 255.

Image data storage means 245 is any means of digital data storage that is compatible with digital signal processor 120 and may be used to store multiple enhanced and/or unenhanced images for future viewing. Examples of such image data storage are random access memory (RAM), read-only memory (ROM), personal computer memory card international association (PCMCIA) memory card, and memory stick. Depending on memory size, hundreds or thousands of separate images may be stored on the image data storage means 245.

Data output 250 is any external device upon which the image data produced by digital signal processor 120 may be viewed, stored, or further analyzed or conditioned. Examples of data output 250 devices include external video displays, external microprocessors, hard drives, and communication networks. Data output 250 interfaces with digital signal processor 120 via interface 52.

Data input 255 is any device through which the user of the system 10 inputs data to digital signal processor 122 in selecting, for example, the appropriate enhancement algorithm, adjusting display parameters, and/or choosing lighting intensity levels. Examples of data input 255 devices include external keyboards, keypads, personal digital assistants (PDA), or a voice recognition system made up of hardware and software that allow data to be inputted without the use of the user's hands. Data input 255 may be an external device that interfaces with digital signal processor 120 via interface 52, or may be integrated directly into the computing unit.

Digital data path 265 is an electronic pathway through which an electronic signal is transmitted from the camera 38 to the digital signal processor 122.

In operation, the infrared imaging system 10 is powered on and the infrared emitters 32, 34 produce the necessary intensity of IR light, preferably at 850 nm and 950 nm wavelengths, required to interact and reflect from oxyhemoglobin and deoxyhemoglobin contained within normal blood. The resulting light path passes through diffuser system 205, where it is dispersed into a beam of uniform incident light 215 of optimal intensity and wavelength. Incident light 215 passes through first polarizers 33, 35, which provide a first plane of polarization. Polarization of incident light 215 reduces the glare produced by visible light by reflection from skin surface 225. Incident light 215 is partially absorbed by the oxyhemoglobin and deoxyhemoglobin that is contained with subcutaneous blood vessels 220 and, thus, produces reflected light 230.

Reflected light 230 passes through second polarizer 39, which provides a second plane of polarization. The second plane of polarization may be parallel, orthogonal, or incrementally adjusted to any rotational position, relative to the first plane of polarization provided by first polarizers 33, 35. Reflected light 230, passes through first lens 240, which provides an image focal length that is appropriate for detection by the camera 38, eliminates all non-near IR light, and reduces interference from other light signals.

Camera 38 detects reflected light 230 and converts it to an electronic digital signal by using CCD, CMOS, or other image detection technology. The resulting digital signal is transmitted to digital signal processor 122 via digital signal path 265. Digital signal processor 122 utilizes a number of algorithms to enhance the appearance of objects that have the spatial qualities of blood vessels, so that the user can distinguish blood vessels easily from other features when Viewed on display 40. Such enhancement might include, for example, image amplification, filtering of visible light, and image analysis. The resulting digital signal is transmitted to display 40 via digital signal path 265, where it is rendered visible by LCD, CRT, or other display technology. Additionally, the resulting digital signal may be outputted to an external viewing, analysis, or storage device via interface 52. The image produced by display 40 is then corrected for depth perception by second lens 260, such that, when the user views the body target area via display 40, the image appears similarly sized and distanced as when the user views the target area with the naked eye.

Figure 5A:
FIG. 5A is an image of a human forearm showing unpolarized visible spectrum light reflected from the forearm and captured by a camera.
Figure 5B:
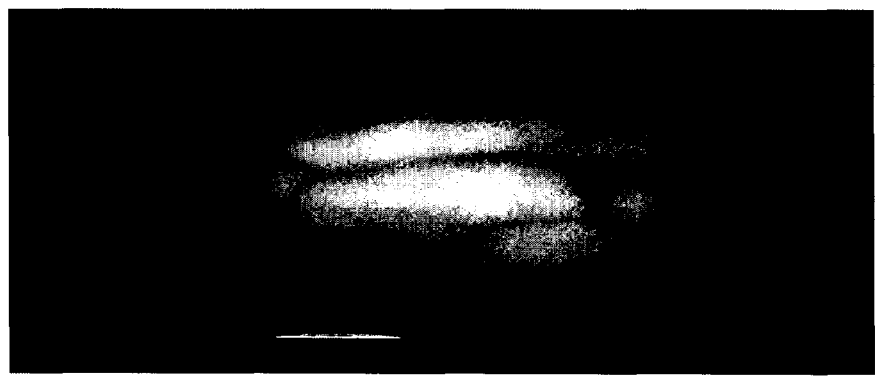
FIG. 5B is a raw image of the human forearm of FIG. 5A showing cross-polarized infrared spectrum light reflected from the forearm and captured by the CMOS camera of the preferred system of the present invention.
Figure 5C:
FIG. 5C is an enhanced image resulting from the operation of the computer program product of the present invention on the raw image of the human forearm of FIG. 5B.

FIGS. 5A, 5B and 5C demonstrate the image enhancement produced by the system of the present invention. FIG. 5A is a photograph of a human forearm using light from the visible spectrum. As seen from this photograph, it is difficult to locate the veins upon visual inspection. FIG. 5B is a raw image of the same human forearm sent from the image capture assembly 30 of the present invention to the processing unit. The veins in this image are considerably more visible than those in FIG. 5A. However, they are not sufficiently dark and well defined to allow easy location of the veins during venepuncture. FIG. 5C is an enhanced image using the image enhancement process of the present invention. As can be seen from this figure, the veins are very dark and, therefore, are easily located for venepuncture.

Figure 6:
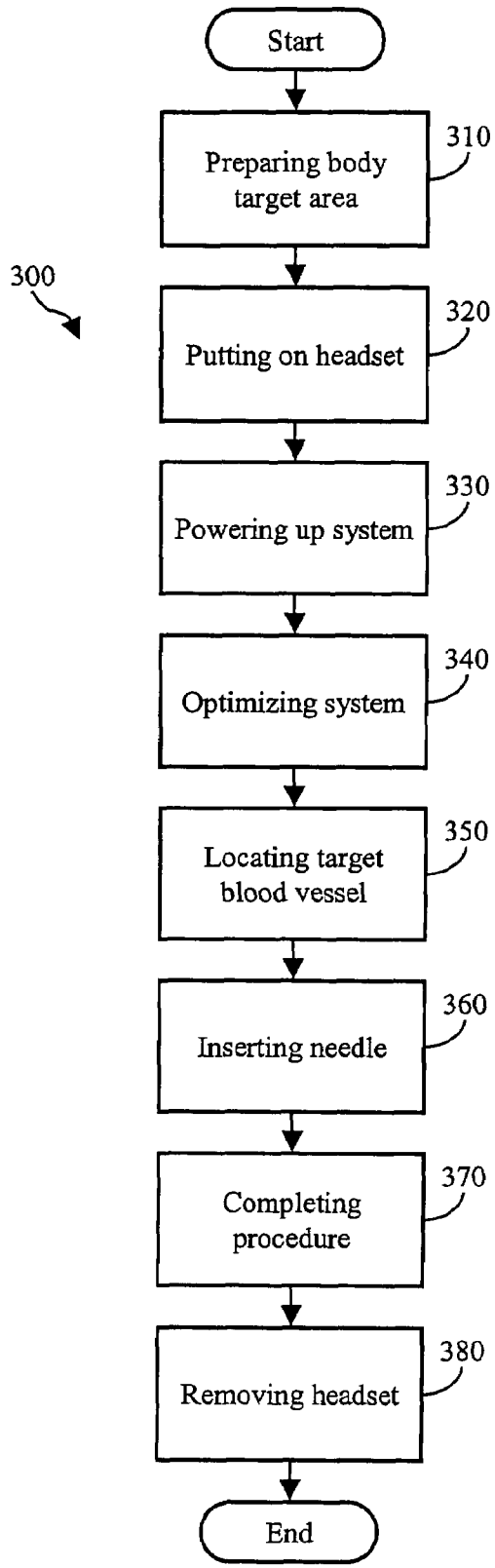
FIG. 6 is a flow diagram of the preferred method of using the system to aid in locating and inserting a hypodermic needle into a blood vessel in accordance with the invention.

FIG. 6 illustrates a flow diagram of a method 300 of using the system 10 to aid in the insertion of a hypodermic needle into a blood vessel in accordance with the invention. Method 300 includes the steps of:

Step 310: Preparing Body Target Area

In this step, a user, such as a medical practitioner (e.g., doctor, nurse, or technician), prepares the patient's body target area for injection by using standard medical practices. This might include, for example, positioning the target body area (e.g., arm), applying a tourniquet, swabbing the target area with disinfectant, and palpating the target area. Method 300 then proceeds to step 320.

Step 320: Putting on the Headset 12

In this step, the user places the headset 12 on his/her head and adjusts head mount 16 for size, comfort, and a secure fit. Method 300 then proceeds to step 330.

Step 330: Powering Up the System

In this step, the user powers up the system 10, by activating a switch controlling the power source 20. Method 300 proceeds to step 340.

Step 340: Optimizing the System

In this step, the user uses data input 255 to adjust various parameters of the system 10, including specifying the appropriate digital signal processor 120 algorithms (according to, for example, the patient's body type, pigmentation, age), intensity levels and/or wavelengths of light produced by the infrared emitters 32, 34, and parameters for the images to be viewed on the display 40. Method 300 then proceeds to step 350.

It should be noted that Steps 320, 330, and 340 may be performed in any order, e.g., the user may power up the system 10 and optimize it, prior to putting it on. Further, it is recognized that a optimizing step 340 may be eliminated altogether, with settings being preset at the factory.

Step 350: Locating Target Blood Vessel

In this step, the user searches non-invasively for the desired target blood vessel(s) (e.g., vein, artery, or capillary bed), by directing the incident light 215 from the infrared emitters 32, 34 on the body target area and viewing the target area on display 40. As viewed on display 40, the target blood vessel(s) will be visually enhanced, i.e., appear darker than the surrounding tissue, which enables the user to insert a hypodermic needle more accurately and rapidly, in order to gain IV access for injection or blood withdrawal. Because of the hands-free operation of the system 10 the user is free to handle the body target area with both hands, for stability, further palpation, and cleansing, for example. Using the system 10 in a bifocal mode, the user may look down from display 40 to see the body target area as it appears under normal, non-enhanced conditions. Based upon a comparison of the image on the display 38 and the unenhanced image viewed in bifocal mode, the user may then adjust the camera lens 24, second lens 260 and/or display 38 to compensate for differences in the enhanced image and unenhanced image. Method 300 proceeds to step 360.

Step 360: Inserting the Needle

In this step, the user, taking advantage of the hand-free operation of system 10, pierces skin surface 225 and inserts a hypodermic needle into the target blood vessel, in order to gain IV access for a procedure, such as, for example, injection or blood withdrawal. Using the enhanced image of the target blood vessel displayed on display 40, the user may pierce the appropriate blood vessel more accurately and rapidly and, thus, save time and money and reduce the patient's physical and emotional pain and trauma. Further, in cases where an infrared viewable needle is used, i.e. one upon which an IR-opaque or IR-reflective substance or pattern is applied, the step also includes the step of viewing the needle position and travel path upon the display. Method 300 proceeds to step 370.

Step 370: Completing Procedure

In this step, the user completes the procedure, for example, drug injection or blood withdrawal process, by using standard medical practices. This may include, but is not limited to, for example, allowing a small amount blood to flow into the syringe, releasing the tourniquet, injecting drugs into the target blood vessel or drawing blood into a capture chamber, and removing the hypodermic needle. Method 300 proceeds to step 380.

Step 380: Removing the Headset 12

In this step, the user removes the headset 12 from his/her head and powers off the system 10. Alternatively, the user prepares additional patients/body target areas for imaging and injection. Method 300 ends.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. An imaging system for locating subcutaneous blood vessels, said system comprising:
    at least one infrared emitter configured to illuminate a region under a surface of a skin with waves of infrared light;
    an infrared detector configured to accept waves of infrared light reflected from the region under the surface of the skin, said infrared detector comprising an output for outputting a signal corresponding to unenhanced image data;
    a computing unit comprising an input for accepting said unenhanced image data, a memory, means for enhancing said unenhanced image data and outputting result images in which enhanced images of blood vessels are shown within images of the region under the surface of the skin, and an output for outputting said enhanced images in substantially real time;
    a display device for inputting said enhanced images from said output of said computing unit and displaying said enhanced images, wherein said display device comprises at least one LCD screen and an optical lens disposed between said LCD screen and an eye of a user;
    a power source in electrical communication with said infrared emitter, said infrared detector, said computing unit and said display device; and
    a headset, wherein said at least one infrared emitter, said infrared detector, said computing unit, said display device, and said power source are attached to said headset, and wherein said display device is disposed such that a user is able to view both said display device and the surface of the skin without removing said headset.

2. The system of claim 1 wherein said means for enhancing and outputting result images comprises a digital signal processing unit programmed with computer program means for enhancing and outputting result images at a rate of at least five frames per second.

3. The system of claim 2 wherein said computer program means comprises:
   program means for Gaussian blurring a raw image with a kernel radius of 15;
   program means for adding an inverse Gaussian-blurred image to the raw image; and
   program means for level adjusting a result image to use an entire dynamic range.

4. The system of claim 1 wherein said at least one infrared emitter comprises two arrays of light emitting diodes.

5. The system of claim 4 wherein said light emitting diodes are surface mounted light emitting diodes comprising integral micro reflectors.

6. The system of claim 5 further comprising at least one light shaping diffuser disposed between said at leastone array of surface mounted light emitting diodes and the surface of the skin.

7. The system of claim 6 further comprising at least one first polarizing filter disposed between said at least one array of surface mounted light emitting diodes and the surface of the skin.

8. The system of claim 7 further comprising at least one second polarizing filter disposed between the surface of the skin and said infrared detector.

9. The system of claim 8 further comprising a camera lens disposed between the surface of the skin and said infrared detector.

10. The system of claim 4 further comprising a pair of extension arms extending from said headset and a mounting surface pivotally attached to said pair of extension arms, and wherein said two arrays of light emitting diodes and said infrared detector are attached to said mounting surface.

11. The system of claim 5 further comprising a pair of extension arms extending from said headset and a mounting surface pivotally attached to said pair of extension arms, wherein said infrared detector comprises a CMOS camera, and wherein said two arrays of surface mounted light emitting diodes and said CMOS camera are attached to said mounting surface.

12. The system of claim 1 further comprising at least one first polarizing filter disposed between said at least one array infrared emitter and the surface of the skin.

13. The system of claim 12 further comprising at least one second polarizing filter disposed between the surface of the skin and said infrared detector.

14. The system of claim 13 further comprising a camera lens, wherein said infrared detector comprises a CMOS camera adapted to generate digital data corresponding to said waves of infrared light reflected from the subcutaneous blood vessels located in the region under the surface of the skin, and wherein said camera lens is disposed between the surface of the skin and said CMOS camera.

15. The system of claim 14 wherein said CMOS camera comprises a high band pass filter adapted to eliminate substantially all light outside of an infrared spectrum from said signal corresponding to said unenhanced image data.

16. The system of claim 1 wherein said display comprises a pair of LCD screens.

17. The system of claim 16 further comprising a pair of optical lenses disposed between said LCD screens and a pair of eyes of a user.

18. The system of claim 1 wherein said infrared detector is a CMOS camera adapted to generate digital data corresponding to said waves of infrared light reflected from the subcutaneous blood vessels located in the region under the surface of the skin.

19. The system of claim 18 further comprising at least one first polarizing filter disposed between said at least one infrared emitter and the surface of the skin.

20. The system of claim 19 further comprising at least one second polarizing filter disposed between the surface of the skin and said CMOS camera.

21. The system of claim 18 further comprising a camera lens disposed between the surface of the skin and said CMOS camera.

22. The system of claim 18 wherein said CMOS camera comprises a high pass filter adapted to filter out substantially all light outside of an infrared spectrum.

23. The system of claim 1 wherein said computing unit further comprises image data storage means for storing multiple images for future viewing.

24. The system of claim 1 wherein said computing unit further comprises an interface and wherein said means for enhancing and outputting result images comprises a digital signal processing unit.

25. The system of claim 24 further comprising a data output in communication with said digital signal processing unit through said interface.

26. The system of claim 25 further comprising a data input in communication with said digital signal processing unit through said interface.

27. The system of claim 24 further comprising a data input in communication with said digital signal processing unit through said interface.

28. The system of claim 1 further comprising a data input, wherein said means for enhancing and outputting result images comprises a digital signal processing unit and wherein said data input is in communication with said digital signal processing unit.

29. A method of using an imaging system to aid in an insertion of a needle into a blood vessel during a performance of a medical procedure, wherein the imaging system comprises a headset, at least one infrared emitter, an infrared detector, a computing unit comprising a digital signal processor and a memory, a power source, a data input, and a display disposed such that a user is able to view both an enhanced image on the display and an unenhanced image on the target area of a surface of a skin of a patient without removing said headset, and wherein said method comprises the steps of:
   preparing a body target area;
   putting on the headset;
   powering up the system;
   optimizing the system, wherein said step of optimizing the system comprises the step of using the data input to specify an enhancement algorithm stored in memory to be used by the digital signal processor to generate the enhanced image;
   locating a target blood vessel by viewing an image of the body target area on the display of the system;
   inserting the needle into the target blood vessel; and performing the medical procedure.

30. The method of claim 29 wherein the infrared detector of the system comprises a camera, and wherein said step of locating a target blood vessel comprises the steps of:
   directing incident light from the infrared emitters on the target area of the surface of the skin; and
   viewing the target area on the display.

31. The method of claim 30 wherein the display comprises an optical lens and wherein said step of locating a target blood vessel further comprises the steps of:
 viewing the image of the target area of the skin as displayed on the display;
 viewing the unenhanced image on the target area of the skin;
 adjusting the optical lens to correct the enhanced image displayed on display for depth perception differences between the enhanced image and the unenhanced image.

32. The method of claim 30 wherein said step of locating a target blood vessel further comprises the steps of:
 viewing the image of the target area of the skin as displayed on the display;
 viewing the unenhanced image on the target area of the skin;
 adjusting the display to correct the enhanced image displayed on display for depth perception differences between the enhanced image and the unenhanced image.

33. The method of claim 29 wherein said step of optimizing the system further comprises the step of selecting an enhancement algorithm based upon a factor selected from a group consisting of a body type, pigmentation, and age of the patient.

34. The method of claim 33 wherein the computing unit comprises a digital signal processor and a memory, wherein the system comprises a data input, and wherein said step of optimizing the system comprises the step of using the data input to adjust an intensity level of the at least one infrared emitter.

35. The method of claim 29 wherein said step of optimizing the system further comprises the step of using said data input to adjust an intensity level of the at least one infrared emitter.

36. The method of claim 29 wherein the needle is an infrared viewable needle and wherein said step of inserting a needle into the target blood vessel further comprises viewing the infrared viewable needle on the display during and after insertion into the target blood vessel.

* * * * *